(12) United States Patent
Woolfson et al.

(10) Patent No.: US 7,402,599 B2
(45) Date of Patent: Jul. 22, 2008

(54) PROTEIN STRUCTURES AND PROTEIN FIBRES

(75) Inventors: Derek N. Woolfson, Sussex (GB); John Walshaw, Sussex (GB); Maya J. Pandya, Sussex (GB); John Colyer, Sussex (GB)

(73) Assignee: The University of Sussex, Sussex (GB)

( * ) Notice: Subject to any disclaimer, the term of this patent is extended or adjusted under 35 U.S.C. 154(b) by 0 days.

(21) Appl. No.: 11/079,139

(22) Filed: Mar. 15, 2005

(65) Prior Publication Data

US 2006/0009620 A1    Jan. 12, 2006

Related U.S. Application Data

(63) Continuation of application No. 10/088,417, filed as application No. PCT/GB00/03576 on Sep. 18, 2000.

(30) Foreign Application Priority Data

Sep. 17, 1999 (GB) ................. 9922013.9
Aug. 28, 2002 (GB) ................. 0219980.0

(51) Int. Cl.
  *A61K 31/44*   (2006.01)
  *A61K 38/00*   (2006.01)
(52) U.S. Cl. .......................... 514/350; 514/2
(58) Field of Classification Search .............. 530/350
See application file for complete search history.

(56) References Cited

U.S. PATENT DOCUMENTS 5,712,366 A * 1/1998 McGrath et al. ............ 530/324

FOREIGN PATENT DOCUMENTS

WO    WO 96/11947    4/1996

OTHER PUBLICATIONS

Kojima et al., "Fibril formation by an amphipathic alpha-helix-forming polypeptide produced by gene engineering," *Proc. of the Japan Academy Series b Physical and Biological*. vol. 73, No. 1. 1997, pp. 7-11.

Petka et al., "Reversible hydrogels from self-assembling artificial proteins," *Science*, Vo. 281, (Jun. 17, 1998), pp. 389-392.

Kohn et al., "De novo design of alpha-helical coiled coils and bundles: models fro the development of protein-design principles," *Trends in Biotechnology*. vol. 16, No. 9, Sep. 1998, pp. 379-389.

L. Gonzalez et al., "Buried Polar Residues and Structural Specificity in the GCN4 Leucine Zipper," Nature Structural Biology 3(12), Dec. 1996, pp. 1011-1018 Abstract.

K. J. Lumb et al., "A Buried Polar Interaction Imparts Structural Uniqueness In a Designated Heteromdimeric Coiled-Coil," Biochemistry 34(27), Jul. 11, 1995, pp. 8642-8648, Abstract.

Derek N. Woolfson et al., "Predicting Oligomerization States of Coiled Coils," Protein Science (1995), 4:1596-1607.

Pehr B. Harbury et al., "A Switch Between Two-, Three-, and Four-Stranded Coiled Coils in GCN4 Leucine Zipper Mutants," Science, Nov. 1993, pp. 1401-1407, vol. 262.

S. A. Potekhin et al., "De Novo Design of Fibrils Made of Short α-Helical Coiled Coil Peptides," Chemistry & Biology 8 (2001) 1025-1032.

Erin K. O'Shea et al., "Peptide 'Velcro': Design of a Heterodimeric Coiled Coil," Current Biology 1993, vol. 3, No. 10, pp. 658-667.

James J. Havranek et al., "Automated Design of Specificity in Molecular Recognition," Nature Structural Biology, Jan. 2003, pp. 45-52, vol. 10 No. 1.

International Preliminary Examination Report of PCT/GB00/03576.
File History of EPC Application 00964388.3.

* cited by examiner

*Primary Examiner*—Cecilia Tsang
*Assistant Examiner*—Maury Audet
(74) *Attorney, Agent, or Firm*—Banner & Witcoff, Ltd.

(57) ABSTRACT

This invention relates to protein fibre formation and in particular to methods of producing protein fibres to form a protein structure comprising a plurality of first polypeptide units arranged in a first polypeptide strand and a plurality of second polypeptide units arranged in a second polypeptide strand, the strands preferably forming a coiled coil structure, and in which a first polypeptide unit in the first strand extends beyond a corresponding second polypeptide unit in the second strand in the direction of the strands.

19 Claims, 10 Drawing Sheets

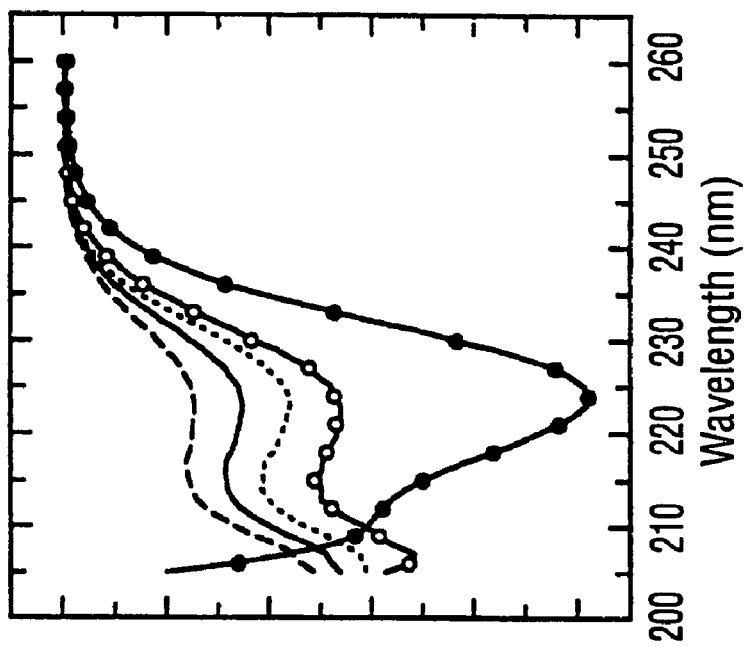
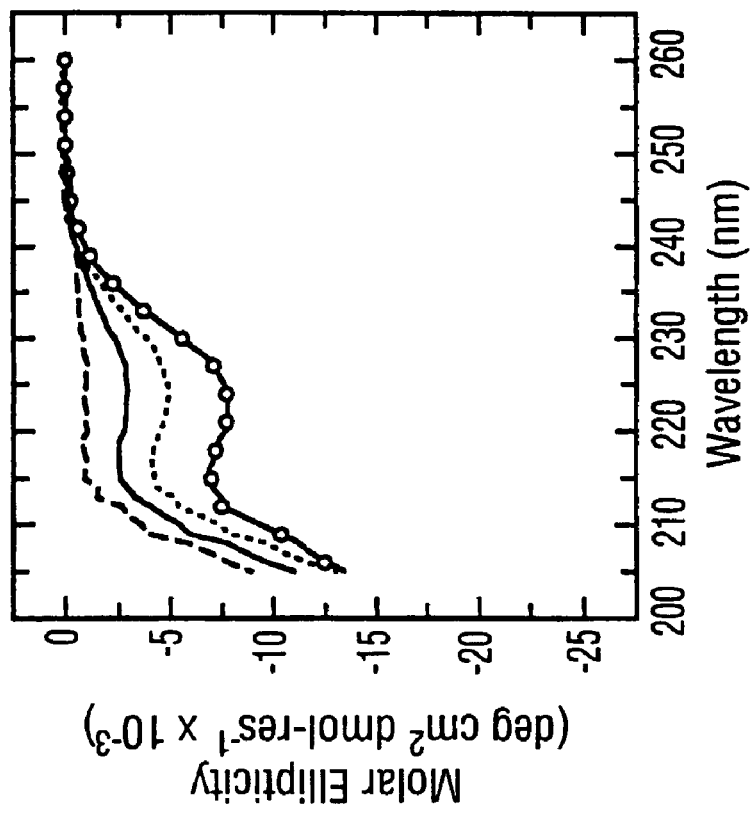
FIG. 3A
FIG. 3B

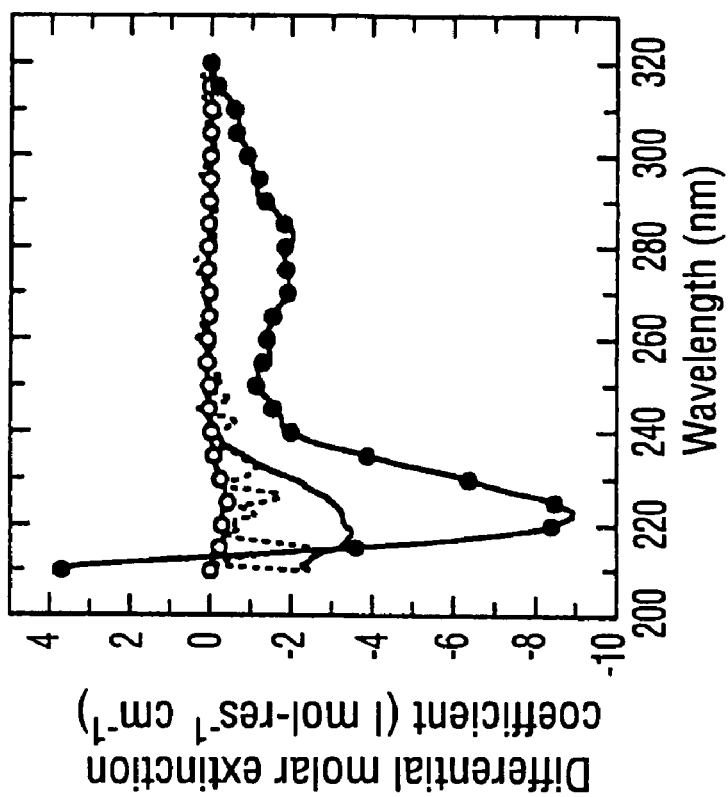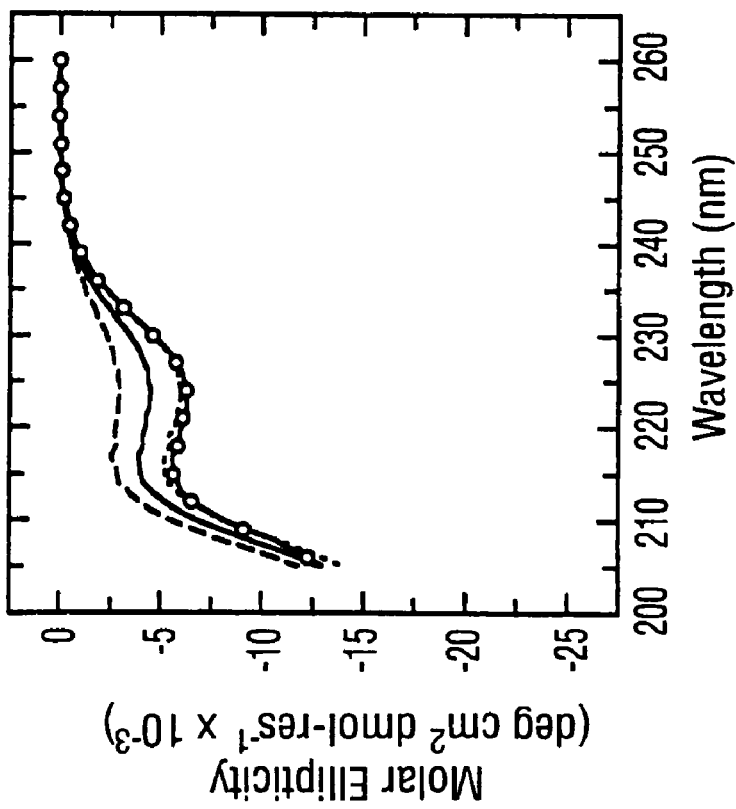
FIG. 3D
FIG. 3C

SEQUENCE LISTING

```
<160> NUMBER OF SEQ ID NOS: 21

<210> SEQ ID NO 1
<211> LENGTH: 28
<212> TYPE: PRT
<213> ORGANISM: Artificial Sequence
<220> FEATURE:
<223> OTHER INFORMATION: synthetic peptides

<400> SEQUENCE: 1

Lys Ile Ala Ala Leu Lys Gln Lys Ile Ala Ser Leu Lys Gln Glu Ile
1               5                   10                  15

Asp Ala Leu Glu Tyr Glu Asn Asp Ala Leu Glu Gln
            20                  25
```

```
<210> SEQ ID NO 2
<211> LENGTH: 28
<212> TYPE: PRT
<213> ORGANISM: Artificial Sequence
<220> FEATURE:
<223> OTHER INFORMATION: synthetic peptides

<400> SEQUENCE: 2

Lys Ile Arg Ala Leu Lys Ala Lys Asn Ala His Leu Lys Gln Glu Ile
 1               5                  10                  15

Ala Ala Leu Glu Gln Glu Ile Ala Ala Leu Glu Gln
            20                  25

<210> SEQ ID NO 3
<211> LENGTH: 28
<212> TYPE: PRT
<213> ORGANISM: Artificial Sequence
<220> FEATURE:
<223> OTHER INFORMATION: synthetic peptides

<400> SEQUENCE: 3

Lys Ile Ala Ala Leu Lys Gln Lys Ile Ala Ala Leu Lys Gln Glu Ile
 1               5                  10                  15

Asp Ala Leu Glu Tyr Glu Asn Asp Ala Leu Glu Gln
            20                  25

<210> SEQ ID NO 4
<211> LENGTH: 28
<212> TYPE: PRT
<213> ORGANISM: Artificial Sequence
<220> FEATURE:
<223> OTHER INFORMATION: synthetic peptides

<400> SEQUENCE: 4

Lys Ile Arg Ala Leu Lys Trp Lys Asn Ala His Leu Lys Gln Glu Ile
 1               5                  10                  15

Ala Ala Leu Glu Gln Glu Ile Ala Ala Leu Glu Gln
            20                  25

<210> SEQ ID NO 5
<211> LENGTH: 18
<212> TYPE: PRT
<213> ORGANISM: Artificial Sequence
<220> FEATURE:
<223> OTHER INFORMATION: synthetic peptides

<400> SEQUENCE: 5

Tyr Gly Pro Gly Glu Ile Ala Ala Leu Glu Gln Glu Asn Ala Ala Leu
 1               5                  10                  15

Glu Gln

<210> SEQ ID NO 6
<211> LENGTH: 28
<212> TYPE: PRT
<213> ORGANISM: Artificial Sequence
<220> FEATURE:
<223> OTHER INFORMATION: synthetic peptides

<400> SEQUENCE: 6

Lys Ile Ala Ala Ile Lys Gln Lys Ile Ala Ala Leu Lys Gln Glu Ile
 1               5                  10                  15

Asp Ala Leu Glu Tyr Glu Asn Asp Ala Leu Glu Gln
            20                  25
```

```
<210> SEQ ID NO 7
<211> LENGTH: 29
<212> TYPE: PRT
<213> ORGANISM: Artificial Sequence
<220> FEATURE:
<223> OTHER INFORMATION: synthetic peptides

<400> SEQUENCE: 7

Lys Ile Ala Ala Leu Lys Gln Ile Cys Ile Ala Ala Leu Lys Gln Glu
 1               5                  10                  15

Ile Asp Ala Leu Glu Tyr Glu Asn Asp Ala Leu Glu Gln
            20                  25

<210> SEQ ID NO 8
<211> LENGTH: 28
<212> TYPE: PRT
<213> ORGANISM: Artificial Sequence
<220> FEATURE:
<223> OTHER INFORMATION: synthetic peptides

<400> SEQUENCE: 8

Lys Ile Ala Ala Leu Lys Gln Lys Ile Ala Ser Leu Lys Gln Glu Ile
 1               5                  10                  15

Asp Ala Leu Glu Tyr Glu Asn Asp Ala Leu Glu Gln
            20                  25

<210> SEQ ID NO 9
<211> LENGTH: 28
<212> TYPE: PRT
<213> ORGANISM: Artificial Sequence
<220> FEATURE:
<223> OTHER INFORMATION: synthetic peptides

<400> SEQUENCE: 9

Lys Ile Ser Ala Leu Lys Trp Lys Asn Ala Ser Leu Lys Gln Glu Ile
 1               5                  10                  15

Ala Ala Leu Glu Gln Glu Ile Ala Ala Leu Glu Gln
            20                  25

<210> SEQ ID NO 10
<211> LENGTH: 28
<212> TYPE: PRT
<213> ORGANISM: Artificial Sequence
<220> FEATURE:
<223> OTHER INFORMATION: synthetic peptides

<400> SEQUENCE: 10

Lys Ile Arg Ala Leu Lys Trp Lys Asn Ala His Leu Lys Gln Glu Ile
 1               5                  10                  15

Ala Ala Leu Glu Gln Glu Ile Ala Ala Leu Glu Gln
            20                  25

<210> SEQ ID NO 11
<211> LENGTH: 29
<212> TYPE: PRT
<213> ORGANISM: Artificial Sequence
<220> FEATURE:
<223> OTHER INFORMATION: synthetic peptides

<400> SEQUENCE: 11

Ile Cys Ile Arg Ala Leu Lys Ala Lys Asn Ala His Leu Lys Gln Glu
 1               5                  10                  15

Ile Ala Ala Leu Glu Gln Glu Ile Ala Ala Leu Glu Gln
```

-continued

```
              20                  25

<210> SEQ ID NO 12
<211> LENGTH: 29
<212> TYPE: PRT
<213> ORGANISM: Artificial Sequence
<220> FEATURE:
<223> OTHER INFORMATION: synthetic peptides

<400> SEQUENCE: 12

Ile Thr Ile Arg Ala Leu Lys Cys Lys Asn Ala His Leu Lys Gln Glu
 1               5                  10                  15

Ile Ala Ala Leu Glu Gln Glu Ile Ala Ala Leu Glu Gln
            20                  25

<210> SEQ ID NO 13
<211> LENGTH: 28
<212> TYPE: PRT
<213> ORGANISM: Artificial Sequence
<220> FEATURE:
<223> OTHER INFORMATION: synthetic peptides

<400> SEQUENCE: 13

Glu Ile Asp Ala Leu Glu Tyr Glu Asn Asp Ala Leu Glu Gln Lys Ile
 1               5                  10                  15

Ala Ala Leu Lys Gln Lys Ile Ala Ser Leu Lys Gln
            20                  25

<210> SEQ ID NO 14
<211> LENGTH: 7
<212> TYPE: PRT
<213> ORGANISM: Artificial Sequence
<220> FEATURE:
<223> OTHER INFORMATION: synthetic peptides

<400> SEQUENCE: 14

Leu Ala Ala Leu Ala Ala Ala
 1               5

<210> SEQ ID NO 15
<211> LENGTH: 43
<212> TYPE: PRT
<213> ORGANISM: Artificial Sequence
<220> FEATURE:
<223> OTHER INFORMATION: synthetic peptides

<400> SEQUENCE: 15

Lys Ile Ala Ala Leu Lys Gln Lys Ile Ala Ser Leu Lys Gln Glu Ile
 1               5                  10                  15

Asp Ala Leu Glu Tyr Glu His His Asp Ala Leu Glu Gln Lys Ile Ala
            20                  25                  30

Ala Leu Lys Gln Lys Ile Ala Ser Leu Lys Gln
        35                  40

<210> SEQ ID NO 16
<211> LENGTH: 42
<212> TYPE: PRT
<213> ORGANISM: Artificial Sequence
<220> FEATURE:
<223> OTHER INFORMATION: synthetic peptides

<400> SEQUENCE: 16

Glu Ile Ala Ala Leu Glu Gln Glu Ile Ala Ala Leu Glu Gln Lys Ile
 1               5                  10                  15
```

-continued

Arg Ala Leu Lys Ala Lys Gln Ala Lys Leu Lys Gln Glu Ile Ala Ala
            20                  25                  30
Leu Glu Gln Glu Ile Ala Ala Leu Glu Gln
        35                  40

<210> SEQ ID NO 17
<211> LENGTH: 29
<212> TYPE: PRT
<213> ORGANISM: Artificial Sequence
<220> FEATURE:
<223> OTHER INFORMATION: synthetic peptides

<400> SEQUENCE: 17

Glu Ile Asp Ala Leu Glu Tyr Glu Gln Asn Asp Ala Leu Glu Gln Lys
1               5                   10                  15
Ile Ala Ala Leu Lys Gln Lys Ile Ala Ser Leu Lys Gln
            20                  25

<210> SEQ ID NO 18
<211> LENGTH: 29
<212> TYPE: PRT
<213> ORGANISM: Artificial Sequence
<220> FEATURE:
<223> OTHER INFORMATION: synthetic peptides

<400> SEQUENCE: 18

Lys Ile Arg Ala Leu Lys Ala Lys Phe Asn Ala His Leu Lys Gln Glu
1               5                   10                  15
Ile Ala Ala Leu Glu Gln Glu Ile Ala Ala Leu Glu Gln
            20                  25

<210> SEQ ID NO 19
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (1)...(1)
<223> OTHER INFORMATION: lysine or glutamate
<220> FEATURE:
<221> NAME/KEY: VARIANT
<222> LOCATION: (2)...(2)
<223> OTHER INFORMATION: isoleucine or asparagine
<220> FEATURE:
<221> NAME/KEY: VARIANT
<222> LOCATION: (3)...(3)
<223> OTHER INFORMATION: alanine or arginine
<220> FEATURE:
<221> NAME/KEY: VARIANT
<222> LOCATION: (6)...(6)
<223> OTHER INFORMATION: lysine or glutamate
<220> FEATURE:
<221> NAME/KEY: VARIANT
<222> LOCATION: (7)...(7)
<223> OTHER INFORMATION: alanine, glutamine, or gluatamate

<400> SEQUENCE: 19

Xaa Xaa Xaa Ala Leu Xaa Xaa
1               5

<210> SEQ ID NO 20
<211> LENGTH: 28
<212> TYPE: PRT
<213> ORGANISM: Artificial Sequence
<220> FEATURE:
<223> OTHER INFORMATION: synthetic
<220> FEATURE:

```
<221> NAME/KEY: VARIANT
<222> LOCATION: (3)...(4)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (7)...(7)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (10)...(11)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (14)...(14)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (17)...(18)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (21)...(21)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (24)...(25)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (28)...(28)
<223> OTHER INFORMATION: alanine, glycine, serine, threonine, cysteine,
      tyrosine, asparagine, glutamine, aspartate,
      glutamate, lysine, arginine, histidine

<400> SEQUENCE: 20

Lys Ile Xaa Xaa Leu Lys Xaa Lys Ile Xaa Xaa Leu Lys Xaa Glu Ile
 1               5                  10                  15

Xaa Xaa Leu Glu Xaa Glu Asn Xaa Xaa Leu Glu Xaa
             20                  25

<210> SEQ ID NO 21
<211> LENGTH: 28
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (3)...(4)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (7)...(7)
<223> OTHER INFORMATION: alanine, glycine, serine, threonine, cysteine,
      tyrosine, asparagine, glutamine, aspartate,
      glutamate, lysine, arginine, histidine
<220> FEATURE:
<221> NAME/KEY: VARIANT
<222> LOCATION: (10)...(11)
<223> OTHER INFORMATION: alanine, glycine, serine, threonine, cysteine,
```

```
        tyrosine, asparagine, glutamine, aspartate,
        glutamate, lysine, arginine, histidine
<220> FEATURE:
<221> NAME/KEY: VARIANT
<222> LOCATION: (14)...(14)
<223> OTHER INFORMATION: alanine, glycine, serine, threonine, cysteine,
        tyrosine, asparagine, glutamine, aspartate,
        glutamate, lysine, arginine, histidine
<220> FEATURE:
<221> NAME/KEY: VARIANT
<222> LOCATION: (17)...(18)
<223> OTHER INFORMATION: alanine, glycine, serine, threonine, cysteine,
        tyrosine, asparagine, glutamine, aspartate,
        glutamate, lysine, arginine, histidine
<220> FEATURE:
<221> NAME/KEY: VARIANT
<222> LOCATION: (21)...(21)
<223> OTHER INFORMATION: alanine, glycine, serine, threonine, cysteine,
        tyrosine, asparagine, glutamine, aspartate,
        glutamate, lysine, arginine, histidine
<220> FEATURE:
<221> NAME/KEY: VARIANT
<222> LOCATION: (24)...(25)
<223> OTHER INFORMATION: alanine, glycine, serine, threonine, cysteine,
        tyrosine, asparagine, glutamine, aspartate,
        glutamate, lysine, arginine, histidine
<220> FEATURE:
<221> NAME/KEY: VARIANT
<222> LOCATION: (28)...(28)
<223> OTHER INFORMATION: alanine, glycine, serine, threonine, cysteine,
        tyrosine, asparagine, glutamine, aspartate,
        glutamate, lysine, arginine, histidine

<400> SEQUENCE: 21

Lys Ile Xaa Xaa Leu Lys Xaa Lys Asn Xaa Xaa Leu Lys Xaa Glu Ile
 1               5                  10                  15

Xaa Xaa Leu Glu Xaa Glu Ile Xaa Xaa Leu Glu Xaa
            20                  25
```

PROTEIN STRUCTURES AND PROTEIN FIBRES

This application is a continuation of U.S. Ser. No. 10/088,417 which is a national phase Application of PCT/GB00/03576 filed Sep. 18, 2000, which was published under PCT Article 21(12) in English and claims the priority of GB 9922013.9.

This invention relates to protein structures, to methods of producing those protein structures, and to protein fibres and other materials and assemblies produced using those protein structures.

The process of molecular self-assembly is central to all biological systems and is assuming increasing importance and application in biotechnology (L. Q. Gu, et al (1999) *Nature* 398, 686) and nanotechnology (K. E. Drexler, (1999) TIBTECH 17, 5). The characterization of natural biomolecular assemblies motivates and directs the development of model self-assembling systems and, in turn, these advance our understanding of biology. For proteins at least, the coiled coil is arguably the simplest self-assembling system. Coiled coils are protein-folding motifs that direct and cement a wide variety of protein-protein interactions (A. Lupas, (1996) *Trends Biochem. Sci* 21, 375). In structural terms, coiled coils are relatively straightforward: they are α-helical bundles with between 2 and 5 strands that can be arranged in parallel, antiparallel or mixed topologies. The basic sequence features that guide the formation of coiled coils from peptides are reasonably well understood (P. B. Harbury et al (1993) *Science* 262, 1401; D. N. Woolfson and T. Alber (1995) *Protein Sci.* 4, 1596). For instance, most coiled-coil sequences are dominated by a 7-residue repeat of hydrophobic (H) and polar (P) residues, $(HPPHPPP)_n$, known as the "heptad repeat". When configured into an α-helix this pattern gives an amphipathic structure, the hydrophobic face of which directs oligomer-assembly. Furthermore, both the number and the direction of chains within a coiled-coil bundle is determined predominantly by residues that form or flank the hydrophobic core namely, residues at the first, fourth, fifth and seventh positions of the heptad repeat. For instance, coiled coils which form dimers (i.e. two-stranded assemblies) usually have isoleucine or valine residues at the first position and a leucine residue at the fourth position. By contrast, coiled coils that form trimers (i.e. three-stranded assemblies) often have the same residues (i.e both isoleucine or both leucine) at both "H" positions. Finally, hetero-oligomers (that is coiled coils made from strands with different amino-acid sequences) may be directed by complementary charged interactions that flank the hydrophobic core. For these reasons, there have been a number of successful de novo protein designs based on the coiled coil These include some ambitious structures that extend the natural repertoire of coiled-coil motifs (S. Nautiyal et al (1995) *Biochemistry* 34, 11645; A. Lombardi et al (1996) *Biopolymers* 40, 495; D. H. Lee et al (1996) *Nature* 382, 525; P. B. Harbury et al (1998) *Science* 282, 1462; J. P. Schneider et al (1998) *Folding Des.* 3, R29).

In addition to commonly accepted structures with a single, contiguous heptad repeat, the inventors have identified sequences with multiple, offset heptad repeats which help explain oligomer-state specification in coiled coils. For example, sequences with two heptad repeats offset by two residues; i.e a/f-b/g'-c/a'-d/b'-e/c'-f/d'-g/e' set up two hydrophobic seams on opposite sides of the helix formed. Such helices may combine to bury these hydrophobic surfaces in two different ways and form two distinct structures: open "α-sheets" and closed "α-cylinders".

Other relevant aspects of coiled-coil structure are described in WO99/11774, the disclosure of which is incorporated herein by way of reference.

This understanding of coiled coils, and the resulting protein designs, centres on short structures as exemplified by the leucine-zipper motifs (E. K. O'shea et al (1989) *Science* 243, 538; E. K. O'shea et al (1991) *Science* 254, 539), which are found in a variety of transcription factors. In contrast, most natural coiled coils extend over hundreds of amino acids (A. Lupas (1996) supra; J. Sodek et al (1972) *Proc. Natl. Acad. Sci. U.S.A* 69, 3800) and many assemble further to form thicker, multi-stranded filaments (H. Herrmann and U. Aebi (1998) *Curr. Opin. Struct. Biol.* 8, 177).

With the goal of making elongated structures to improve our understanding of coiled coils, and to develop protein-design studies, we initially designed two 28-residue peptides—dubbed Self-Assembling Fibre peptides, SAF-p1 and SAF-p2—to fold and form extended fibres when mixed. Focusing on the buried, hydrophobic-core positions of the structure, rules were incorporated to direct parallel dimer formation and to guard against alternative oligomers and topologies (P. B. Harbury et al (1993) supra; D. N. Woolfson and T. Alber (1995) supra; L. J. Gonzalez et al (1996) *Nature Struct. Biol.* 3, 1011). The building block of the design was a staggered heterodimer with overhanging or "sticky" ends. This contrasts with and distinguishes it from the natural and designer coiled-coil assemblies that have been characterized to date, in which the polypeptide strands align in-register, i.e they have blunt or "flush" ends. Complementary core interactions and flanking ion-pairs were incorporated into the overhangs to facilitate longitudinal association of the heterodimers (FIGS. 1 & 2). This principle of using "sticky ends" is well developed in molecular biology for assembling DNA (S. J. Palmer et al (1998) *Nucleic Acids Res.* 26, 2560), and has been used to design intricate DNA crystals (E. Winfree et al (1998) *Nature* 394, 539). However, to our knowledge, our application of sticky end-directed molecular assembly to peptides is new; although we do note that head-to-tail packing of helices has been observed in recently solved crystal structures for two designer peptides (N. L. Ogihara et al (1997) *Protein Sci.* 6, 80; G. G. Prive et al (1999) *Protein Sci.* 8, 1400). These were helical peptides that crystallised with their helical ends in contact so as to form pseudo-continuous helices in the solid state. In other words they formed "blunt-ended" arrangements.

According to one aspect of the invention there is provided a protein structure comprising a plurality of first peptide monomer units arranged in a first strand and a plurality of second peptide monomer units arranged in a second strand, the strands preferably forming a coiled-coil structure, and in which a first peptide monomer unit in the first strand extends beyond a corresponding second peptide monomer unit in the second strand in the direction of the strands. The protein structures of the invention have numerous advantages. For example, relatively long protein fibres can be formed with little material—1 μl of a 100 μM solution of the peptide monomers may provide enough material to form 10 m of fibre 50 nm thick.

At least one charged amino acid residue of the first peptide monomer unit may be arranged to attract an oppositely-charged amino acid residue of the second peptide monomer unit. Preferably, the charged amino acid residue is in an end portion of the first peptide monomer unit, which extends beyond the corresponding second peptide monomer unit in the second strand. At least one strand may consist solely of first or second peptide monomer units respectively i.e homogenous strands. Heterologous strands are also contemplated.

The peptide monomer units may comprise a repeating structural unit. Preferably, the repeating structural unit comprises a heptad repeat motif, having the pattern:

```
hppdppp abcdefg
```

Preferably, the repeat may include isoleucine or asparagine at position a and leucine at position d. Other repeats (e.g hendecads—abcdefghijk) and amino acid compositions may also be used (see WO99/11774).

Preferably, the heptad repeat comprises oppositely-charged residues at positions e and g respectively. The oppositely-charged residues may be, for example, glutamic acid and lysine residues or arginine and aspartic acid. The use of synthetic amino acids, such as ornithine is also envisaged.

A protein structure in accordance with the invention may be also specified by pairs of asparagine residues in the "a" positions provided by corresponding first and second peptide monomer units.

In a preferred protein structure, the first and second peptide monomer units have the following sequences:
a) KIAALKQKIASLKQEIDALEYENDALEQ (SAF-p1C) and
b) KIRALKAKNAHLKQEIAALEQEIAALEQ (SAF-p2D) respectively; or
c) KIAALKQKIAALKQEIDALEYENDALEQ (SAF-p1A) and
d) KIRALKWKNAHLKQEIAALEQEIAALEQ (SAF-p2C) respectively; or
e) KIAALKQKIASLKQEIDALEYENDALEQ (SAF-p1C) and
f) KIRALKWKNAHLKQEIAALEQEIAALEQ (SAF-p2C) respectively.

It will be appreciated that these are examples only of 4-heptad structures and that other lengths are possible and envisaged for use in the invention.

According to another aspect of the invention, there is provided a method of producing protein structures, the method comprising providing a mixture of first and second peptide monomer units which associate to form a protein structure according to the invention. The structure can be derivatised and/or stabilized by cross-linking.

Derivatization of the peptide monomer units before or after assembly into the protein structures of the invention may be performed. For example, fluorescent moieties (fluorophores) may be attached to the coiled coil as described in WO99/11774. The addition of fluorescent moieties may assist visualization of the protein structure. Substitution with functional groups at the "f" position in the heptad repeat is especially preferred as that position is on the outside of the helix (see FIGS. 1C and 1E). Other derivatives may include attaching binders to the peptide monomer units for example so that units which can bind other entities can be produced.

The first and second peptide monomers and the strands may have the characteristics described above.

The invention also provides protein fibres produced by an association of protein structures according to the invention.

The protein structures may also be arranged to form tubular structures. In particular, the structures may be arranged to form nanotubes.

According to another aspect of the invention, there is provided a kit for making protein structures, the kit comprising first and second peptide monomer units which associate to form a protein structure or protein fibres according to the invention.

The protein structures of the invention may be assembled in two and three dimensional arrays. For example, two dimensional mats can be formed which can flimction, for example as filters. Three dimensional grids or matrices can also be formed again, for example, for use as sieves or filters or for organising other associated or conjugated molecules in three dimensions.

In a preferred embodiment, a matrix is assembled in situ. For example, a matrix can be formed in a solution to entrap contaminants in the solution and then the matrix, together with contaminants, can be removed from the solution for example by centrifugation.

The stability of the protein structures at higher temperatures may be improved by making the peptide monomers longer, such that the overlap between corresponding first and second monomer unit residues is increased. Increases in monomer length have previously been shown to stabilize coiled coil structures. Alternatively, stability can be improved by introducing bonding between adjacent peptide monomer units in the same strand. For example, Kent (Dawson et al (1994) *Science* 266: 776) and co-workers have produced peptide bonds between adjacent polypeptide units by coupling and subsequent rearrangement of a cysteine residue at the N end of one polypeptide unit to a thio-ester derivatised C-terminus of another unit.

Additionally, the protein structures may be stabilised and derivatised by using them to template the polymerisation of synthetic polymers.

Definitions

The terms used in the specification are to be given the ordinary meaning attributed to them by the skilled addressee. The following is given by way of clarification:

Amino Acid

This term embraces both naturally-occuring amino acids and synthetic amino acids as well as naturally-occuring amino acids which have been modified in some way to alter certain properties such as charge. In all cases references to naturally-occurring amino acids may be considered to include synthetic amino acids which may be substituted therefor.

Coiled Coil

A coiled-coil is a peptide/protein sequence usually with a contiguous pattern of hydrophobic residues spaced 3 and 4 residues apart, which assembles (folds) to form a multi-meric bundle of helices. Coiled-coils including sequences with multiple offset repeats are also contemplated.

Dimer

A dimer is a two stranded structure.

Heterodimer

A heterodimer is a dimeric structure formed by two different stands.

Staggered Heterodimer

A staggered heterodimer is a structure in which the two strands assemble to leave overlapping ends that are not interacting within the heterodimer.

Blunt-end Assembly

Blunt-end assembly is association where the two strands combine to give flushed i.e non-overlapping ends.

Protofibril

A protofibril is a protein structure assembled longitudinally from staggered heterodimers interacting through their overhanging ends.

Fibre

A fibre is a structure formed by lateral association of two or more protofibrils.

Protein structures and methods of producing protein structures in accordance with the invention will now be described, by way of example only, with reference to the accompanying FIGS. 1 to 8 in which:

FIG. 3 illustrates the results of circular dichroism (CD) and linear dichroism (LD) experiments on protein structures of the invention.

1) PEPTIDE DESIGN AND SYNTHESIS

Various peptide monomer units were designed as described above. The monomers and capping peptides (designed to complement the sticky ends of the monomers so as to produce flush, or blunt ends and, so, arrest longitudinal fibre assembly) are set out in Table 1:

TABLE 1

| PEPTIDE | SEQUENCE g abcdefg abcdefg abcdefg abcdef  5      10     15     20     25 | DESIGN | CD DATA @ 10 μM | CD DATA @ 100 μM | LD DATA @ 10 μM | LD DATA @ 100 μM | EM DATA @ 10 μM | EM DATA @ 100 μM |
|---|---|---|---|---|---|---|---|---|
| CAP-p1A |   *YGPGE IAALEQE NAALEQ | prototype | unfolded | | | | | |
| SAF-p1A | K IAALKQK IAALKQE IDALEYE NDALEQ | prototype; slowly precipitates | unfolded | ~45% α-helix | | | | no fibres |
| SAF-p1B | *K IAALKQK IAALKQE IDALEYE NDALEQ* | chemical capping of the ends (↑ stability) | ~60% α-helix | ~70% α-helix | | | | |
| SAF-p1C | K IAALKQK IASLKQE IDALEYE NDALEQ | no capping (↓ stability); mutate $A_{11} \rightarrow S$ (↑ solubility & ↓ helix stability) | unfolded | ~20% α-helix | | no signal | | no fibres |
| CAP-p2A | K IAALKQK NAALKQG GW* | prototype | unfolded | | | | | |
| SAF-p2A | K ISALKWK NASLKQE IAALEQE IAALEQ | prototype; low solubility | unfolded | | | | | |
| SAF-p2B | *K IRALKWK NAHLKQE IAALEQE IAALEQ* | mutate $S_3 \rightarrow R$ & $S_{11} \rightarrow H$ (↑ solubility & ↑ helix stability) | ~60% α-helix | ~95% α-helix | | | | |
| SAF-p2C | K IRALKWK NAHLKQE IAALEQE IAALEQ | no capping (↓ stability) | unfolded | ~20% α-helix | | | | thin fibres |
| SAF-p2D | K IRALKAK NAHLKQE IAALEQE IAALEQ | mutate $W_7 \rightarrow A$ (investigate role of Trp in fibrillogenesis) | ~15% α-helix | ~45% α-helix | | no signal | | no fibres |
| SAF-p2E | K IRALKCK NAHKQE IAALEQE IAALEQ | mutate $A_7 \rightarrow C$ (for derivatization & cross-linking) | | | | | | |

*= Chemical capping = $CH_3CO$ at the N terminus and $NH_2$ at the C terminus

FIG. 4 illustrates the assembly of synthetic protein fibres visualized directly by transmission electron microscopy and an analysis of fibre width In all panels, the white scale bars represent 100 nm. FIG. 4D is a histogram showing the distribution of fibre widths determined using TEM for fresh (white bars) and matured (black bars) mixtures of SAF peptides at 100 μM (a width value of "x" on the histogram includes all measurements made from "(x−5) to x").

Figure 5:
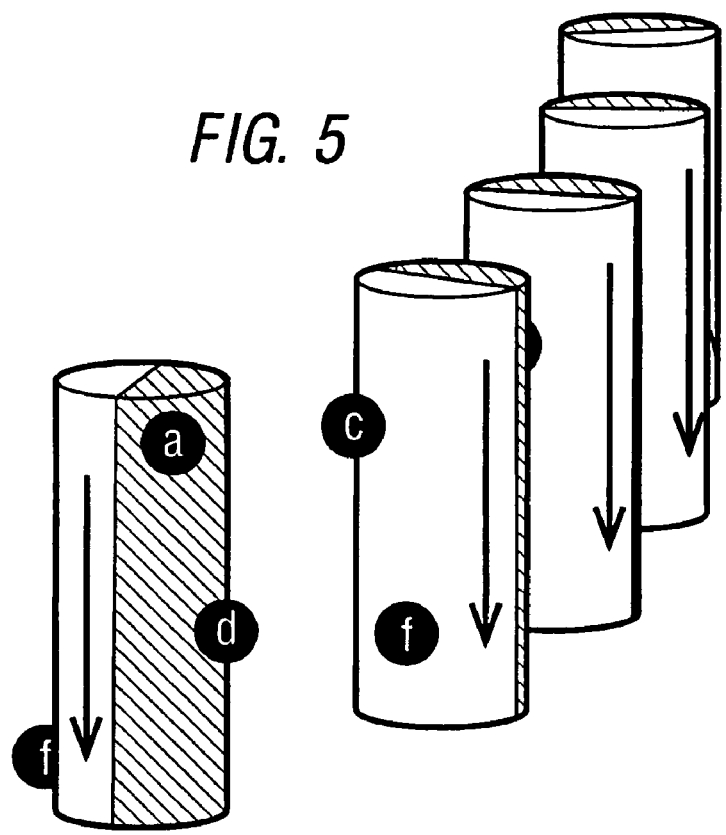

FIG. 5 is a cartoon showing the possible anti-typic association of parallel helical peptides leading to a homo-oligomeric peptide nanotube.

Figures 1A, 1B:
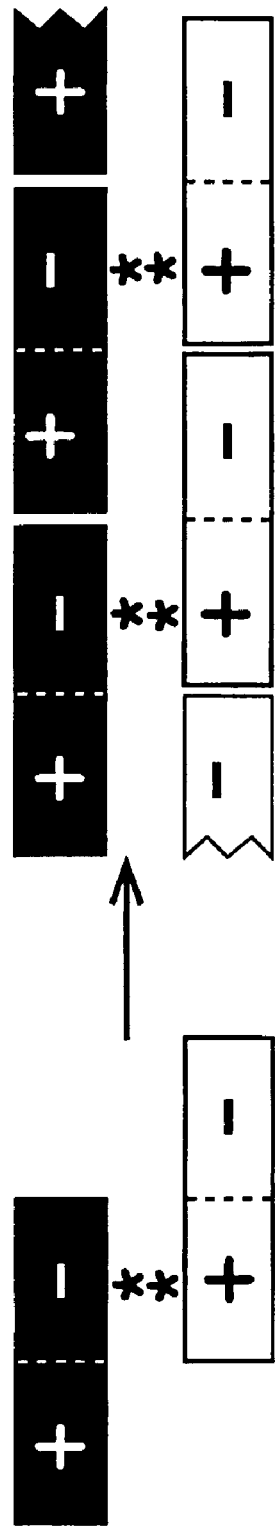
FIG. 1 illustrates the design and the sequences of self-assembling fibre (SAF) peptide monomers of the invention.
Figure 1C:
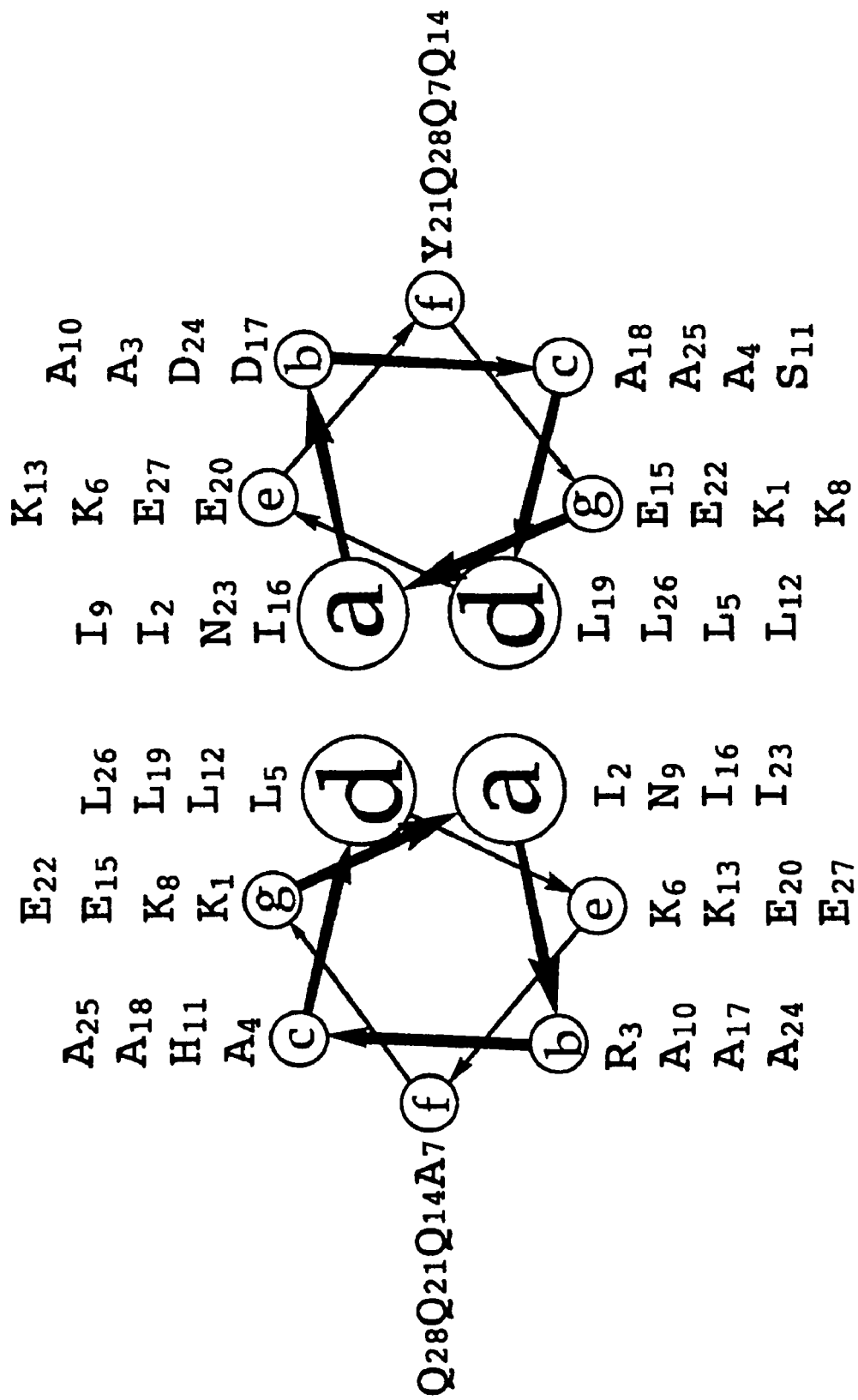

FIG. 1 shows (A) A mechanism for self-assembly: complementary charges in "companion" peptides direct the formation of staggered, parallel heterodimers; the resulting "sticky" ends are also complementary and promote longitudinal association into extended structures. FIG. 1(B) shows the designed amino acid sequences: each peptide comprised canonical heptad repeats (abcdefg) with Ile at a and Leu at d to guide the formation of coiled-coil dimers; oppositely-charged residues were incorporated at e and g to favour the staggered dimer with sticky ends; asparagine residues (which preferentially pairs with each other at a sites (Gonzalez L et al (1996) *Nature Structural Biology* 3, 13: 1011-1018) were included to cement the prescribed register further and to favour the parallel structures. FIG. 1(C) is a helical-wheel representation, summarizing the designed sequences in context. The view is from the N-terminus with heptad sites labeled a-g and assumes 3.5 residues per helical turn to emphasise the heptad repeat.

The peptides were synthesized on an Applied Biosystems 432A Peptide Synthesizer using solid-phase methods and Fmoc chemistry. Peptide samples were purified using reversed-phase HPLC and their identities confirmed by MALDI-TOF mass spectrometry.

Figure 2A:
FIG. 2 illustrates computer modelling of the designed self-assembling fibre of the invention.
Figure 2B:
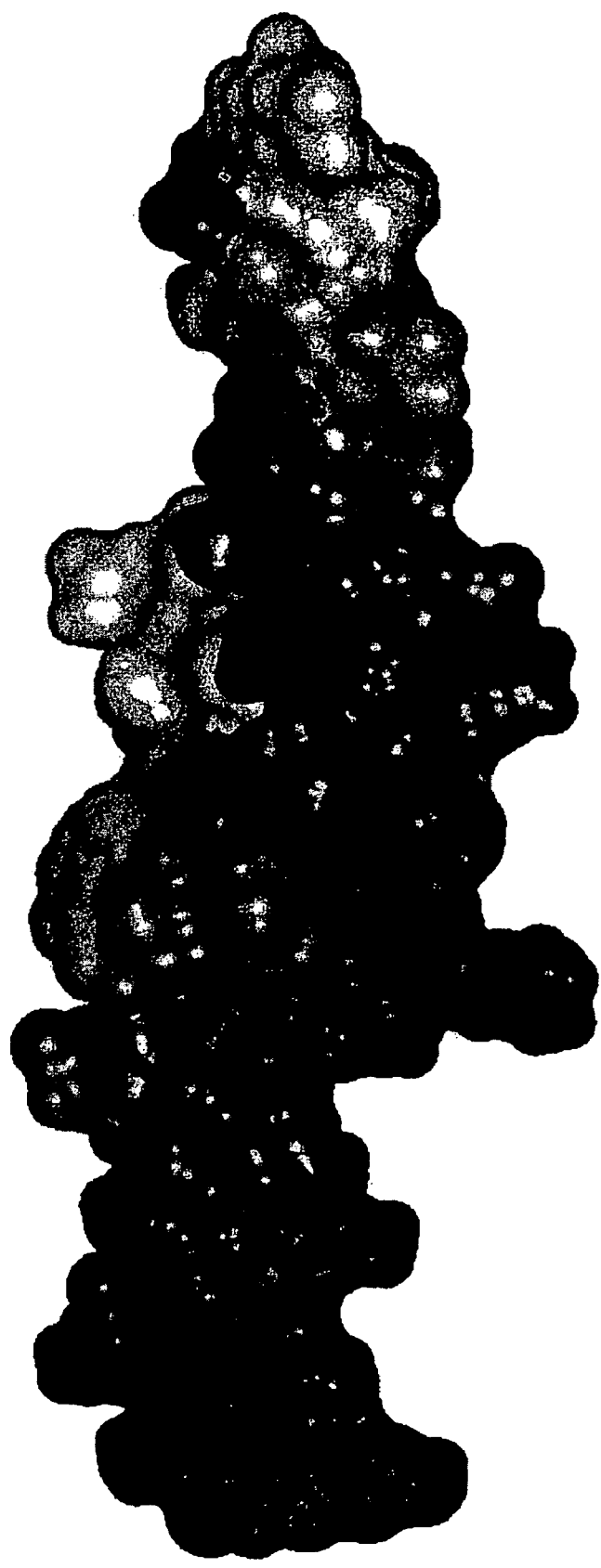

Various combinations of peptide monomers and capping peptides were tested as set out in Table 2:

in FIG. 1B. The structure was soaked in a 5 Å layer of water and energy minimised until the average absolute derivative of coordinates with respect to energy fell below 0.01 kcal Å$^{-1}$. The structure was built and visualized using Insight II 97.0 (Molecular Simulations Inc.), and was energy-minimized using Discover 2.9.8 (Molecular Simulations Inc.) with the consistent valence forcefield. In FIG. 2(A) peptides SAF-p1 and SAF-p2 (each coloured dark grey-to-light grey from the N-terminus) interact through core residues including asparagine pairs (coloured mid-grey) to form the two strands of a staggered, parallel, coiled-coil fibre. In FIG. 2(B), negatively charged glutamate side chains (coloured light grey) and posi-

TABLE 2

| MISC. | PEPTIDE MIXTURE | EQUILIBRATION | CD DATA @ 10 μM | CD DATA @ 100 μM | LD DATA @ 10 μM | LD DATA @ 100 m μM | EM DATA @ 10 μM | EM DATA @ 100 μM |
|---|---|---|---|---|---|---|---|---|
| no signal from fibres in 1D-NMR | SAF-p1A, SAF-p2A | | ~20% α-helix | ~40% α-helix $T_m \approx 30°$ C. | | | | |
| | SAF-p1A, SAF-p2A, CAP-p1A, CAP-p2A | | | ~20% α-helix | | | | |
| | SAF-p1A, SAF-p2B | rapid | | ~65% α-helix $T_m \approx 36/46°$ C. (expect 38° C. if no interaction) | | | | |
| | SAF-p1B, SAF-p2B | rapid | ~70% α-helix $T_m \approx 25°$ C. (expect 19° C. if no interaction) | ~80% α-helix $T_m \approx 35°$ C. (expect 36° C. if no interaction) | | | | no fibres |
| | SAF-p1A, SAF-p2C | slow @ 100 μM; clouding occurs | ~20% α-helix | ~80% α-helix biphasic thermal melt | | | no fibres | thick fibres (~45 nm wide) |
| | SAF-p1C, SAF-p2C | slow @ 100 μM; clouding occurs | ~25% α-helix | ~65% α-helix (~25% in 0.5 M salt); unusual spectral shape; no aromatic signal | no signal | strong signal from backbone & aromatics | no fibres | thick fibres (~45 nm wide); no fibres in 0.5 M salt |
| | SAF-p1C, SAF-p2D | slow @ 100 μM; clouding occurs | ~25% α-helix | ~85% α-helix (~20% in 0.5 M salt); unusual spectral shape | no signal | strong signal from backbone & aromatics; no signal in 0.5 M salt | no fibres | thick fibres (~45 nm wide); no fibres in 0.5 M salt |

Indicates large structures are formed.

In addition and as a control, the SAF-p1c sequence was permuted (N- and C-terminal halves were swapped) to produce peptide SAF-p3:

E IDALEYE NDALEQK IAALKQK IASLKQ

This design should combine with SAF-p2D to form a blunt-ended structure, which should not form fibres.

2) Modeling of Protein Fibre Structure

A model of the three-dimensional structure of the designed protein fibre resulting from the assembly of SAF-p1 and SAF-p2 was made from the minimised structure of a model coiled-coil 35-mer, (LAALAAA)$_5$, which was generated using Crick's Equation and had an ideally packed interface (G. Offer and R. Sessions, *J. Mol. Biol.* 249, 967 (1995)). Copies of the 35-mer were superimposed with an overlap of one heptad repeat to extend the structural template, and the backbone was rejoined after removal of overlapping segments. Residues in the two-stranded template were replaced with the sequences of the SAF peptides, staggered relative to each other by two heptad repeats according to the alignment tively charged lysine side chains (coloured black) form complementary charge interactions between the SAF peptides.

3) Circular Dichroism Experiments

Peptide samples were incubated at 5° C. in 10 mM MOPS (3-(N-Morpholino)propanesulfonic acid), pH 7. Sample concentrations were determined from their UV absorbance at 280 nm (SAF-p1) and 214 nm (SAF-p2). After baseline correction, ellipticities in mdeg were converted to molar ellipticities (deg cm$^2$ dmol-res$^{-1}$) by normalizing for the concentration of peptide bonds. Data were recorded in a cell of 1 mm path length by integrating the signal for 5 s (and 1 s for the fresh 100 μM peptide mixture) every nm in the range 205-260 nm. CD measurements were made using a JASCO J-715 spectropolarimeter fitted with a Peltier temperature controller.

The CD data shown in FIG. 3 provides spectroscopic evidence for the formation of helical structures by the SAF peptides. FIG. 3(A) shows circular dichroism (CD) spectra at 10 μM for: SAF-p1 ( - - - ), SAF-p2 ( - - - ), the average of these spectra ( - - - ), and the experimental SAF peptide mixture (o). FIG. 3(B) shows CD spectra at 100 μM—the key is the same as for FIG. 3(A), but with the additional spectrum (•) being for the SAF peptide mixture after "maturation" for 1 h.

Consistent with our design, neither SAF-p1 nor SAF-p2 was highly structured in aqueous solution at pH 7 and 5° C. (FIG. 3). However, when mixed in equal proportions the circular dichroism (CD) spectrum changed and, moreover, was markedly different from the theoretical spectrum generated by averaging the spectra for the isolated peptides. In particular, the spectrum for the mixture had intense minima at 208 and 222 nm consistent with the formation of α-helical structure, but these features were not as pronounced in the spectra of the individual peptides. This was clear evidence that the two peptides interacted to form an α-helical structure as designed. Furthermore, and as expected for a multimerization event, the magnitude of these spectral changes depended on peptide concentration; a SAF mixture with 10 μM of each peptide, did show a weak signal indicative of some α-helical structure, however, a 100 μM mixture gave a much stronger signal (FIGS. 3A & B).

The shape and intensity of spectra from 100 μM mixtures of the SAF peptides also changed with time (FIG. 3B). Spectra recorded immediately after mixing a "fresh" sample displayed some α-helical structure. After incubation of the mixture for 1 hour at 5° C. ("maturation"), however, the signal at 222 nm was more intense, and indicated approximately 75% α-helix, consistent with substantial coiled-coil formation.

Maturation of 100 μM SAF peptide mixtures was also accompanied by slight clouding of the samples. Scattering effects from such samples can lead to attenuation and distortion of CD spectra (D. Mao and B. A. Wallace, (1984) *Biochemistry* 23, 2667). However, we could disregard this possibility because altering the distance between the sample and the detector in the CD instrument did not affect the shape or the intensity of the spectrum. Furthermore, we established that the majority of the CD signal from the mixtures derived from the suspended material: a supernatant without the suspended material, which was recovered by centrifugation of a matured 100 μM SAF mixture, gave only a weak CD signal similar to the 10 μM mixture.

Thus, the CD data were wholly consistent with the desired α-helical SAF design and, moreover, indicated the formation of large assemblies.

As a control, SAF-p3 (the permutation of SAF-p1 (identical to SAF-p1c)) was designed to form a blunt-ended heterodimer with SAF-p1 that should not assemble further into fibres. 100 μM mixtures of SAF-p2 (identical to SAF-p2D) and SAF-p3 were analysed by sedimentation equilibrium in the analytical ultracentrifuge. The resulting data were best fitted assuming a single ideal species in solution, and the molecular weight was allowed to vary during the fit. An $M_r$ of 6422 (with 95% confidence limits of 5924 and 6911) was obtained, which is very close to the expected heterodimer value of 6303 calculated from mass spectrometry of the individual peptides. CD spectra for 100 μM fibre-producing mixtures (SAF-p1 with SAF-p2), and for blunt dimer-producing mixtures (SAF-p2 with SAF-p3), were recorded. For the blunt dimer-producing mixtures, the shape and intensity of the CD spectrum were fully consistent with coiled-coil formation as designed. In contrast to the fibre-producing mixtures, the blunt dimer-producing mixtures showed no signs of maturation; that is, negligible spectral changes and no clouding of solutions occurred upon incubation. Interestingly, the intensity of the minimum near 222 nm, which is an accepted indicator of α-helical structure and degree of α-helical folding, was similar for both mixtures. This strongly supports the formation of α-helical structure as designed in the fibre-producing mixtures despite the spectral shifts observed upon maturation.

4) Linear Dichroism Experiments

Linear dichroism (LD) spectroscopy was also used to test if elongated structures were being formed as designed. Long polymers such as DNA molecules can be oriented by shear flow. This effect can be monitored by LD spectroscopy provided that chromophores also become aligned by the flow (M. Bloemendal (1994) *Chem. Soc. Rev.* 23, 265; A. Rodger and B. Norden (1997) Oxford Chemistry Masters (Oxford University Press, Oxford), vol. 1).

Peptide samples were prepared for LD as for CD. LD data were collected on samples spinning in a couette flow cell by integrating the signal for 2 s every nm in the range 210-320 nm, using a JASCO J-715 spectropolarimeter. After baseline correction, absorbance was converted to molar extinction coefficient (1 mol-res$^{-1}$ cm$^{-1}$) by normalizing for the concentration of peptide bonds. A linear correction for a sloping baseline was made to the data from the 100 μM SAF peptide mixture.

The results are depicted in FIG. 3D, which shows linear dichroism (LD) spectra for: 20 μM tropomyosin ( - - - ), the SAF peptide mixture at 10 μM ( - - - ), and the SAF peptide mixture at 100 μM in the absence (•) and presence (o) of 0.5 M KF.

For instance, we found that tropomyosin, which forms a dimeric coiled coil approximately 42 nm in length, could be aligned to give a LD signal (FIG. 3D). In contrast and consistent with our design and the CD data, experiments with a 10 μM SAF mixture, (FIG. 3D), and for the individual peptides at 100 μM (data not shown), LD signals were not detected. However, a matured 100 μM SAF peptide mixture gave a strong absorbance from the peptide backbone (210-240 nm) and some signal in the aromatic region (260-290 nm) during flow orientation (FIG. 3D). As only long structures are aligned by this technique, the data demonstrated that long fibres at least 500 nm in length were present in solutions of the matured 100 μM SAF peptide mixtures.

5) Electron Microscopy

To confirm fibre assembly, we used electron microscopy to visualize structures in the peptide preparations directly. For TEM experiments, peptide samples were incubated for 1 h at 5° C. in filtered 10 mM MOPS, pH 7. A drop of peptide solution was applied to a carbon-coated copper specimen grid (Agar Scientific Ltd, Stansted, UK), and dried with filter paper before negative staining with 0.5% aqueous uranyl acetate and then dried at 5° C. A "fresh" SAF peptide mixture was prepared by mixing preincubated solutions of the individual peptides at 200 μM directly on the specimen grid, before drying and negative staining as described. Grids were examined in a Hitachi 7100 TEM at 100 kV and digital images were acquired with a (800×1200 pixel) charge-coupled device camera (Digital Pixel Co. Ltd., Brighton, UK) and analyzed (Kinetic Imaging Ltd., Liverpool, UK).

For scanning electron microscopy (SEM) experiments, negatively-stained specimen grids were sputter-coated with gold and examined in a Leo Stereoscan 420 SEM at 20 kV and with a probe current of 10 pA.

Figure 4B:
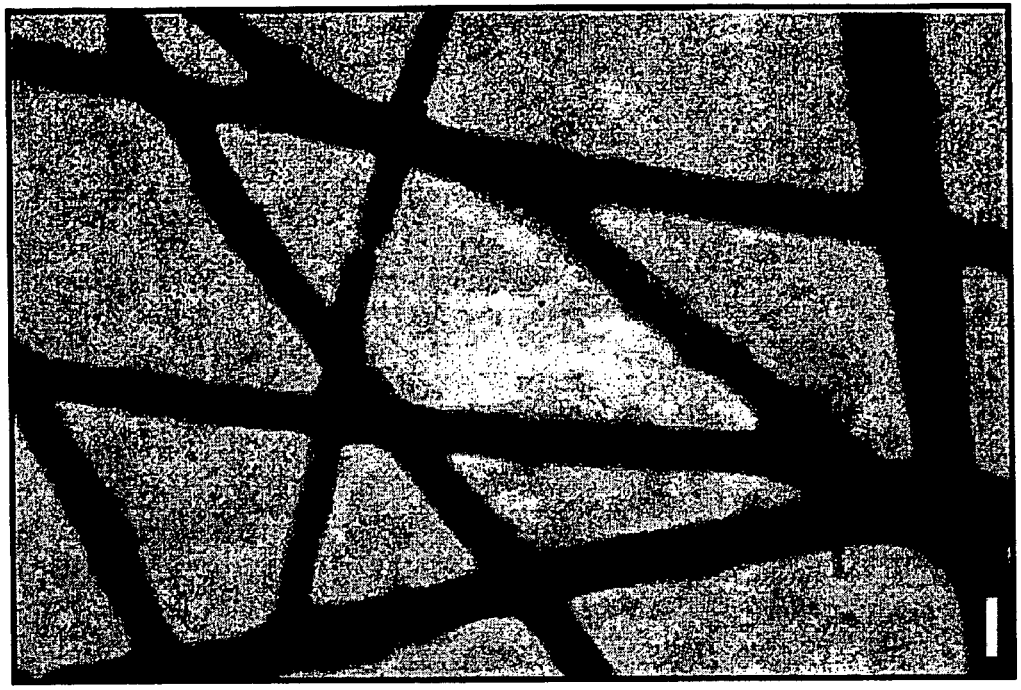
Figure 4A:
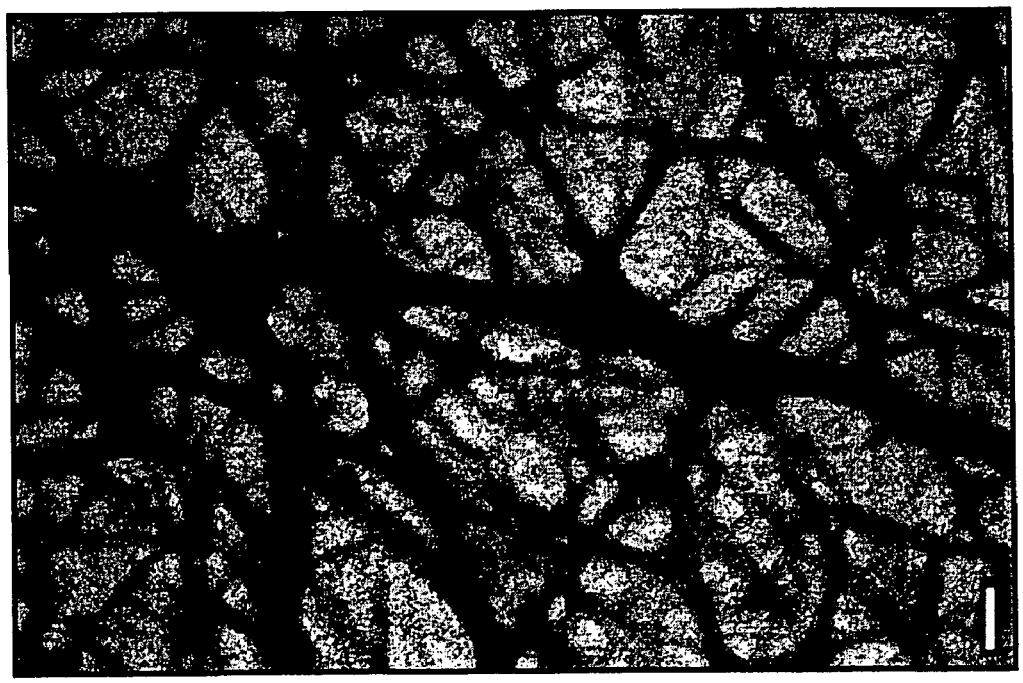

No structures were visible up to 100 000 times magnification by transmission electron microscopy (TEM) for either the 10 μM SAF mixture, or for the individual peptides at 100 μM concentration (data not shown). However, TEM of a 100 μM SAF mixture at 50 000 times magnification revealed time-dependent formation of long fibrous structures, consistent with the CD and LD data. Fresh mixtures showed large numbers of extended fibres of various widths. The majority of these had a diameter of about 20 nm (FIG. 4A (a fresh mixture at 100 μM) & FIG. 4D); finer fibres were present, but their widths could not be measured reliably. Images recorded for the matured mixtures showed fewer fibres, but these were more distinct and thicker than those observed in the fresh mixture (FIGS. 4B & D).

Figure 4E:
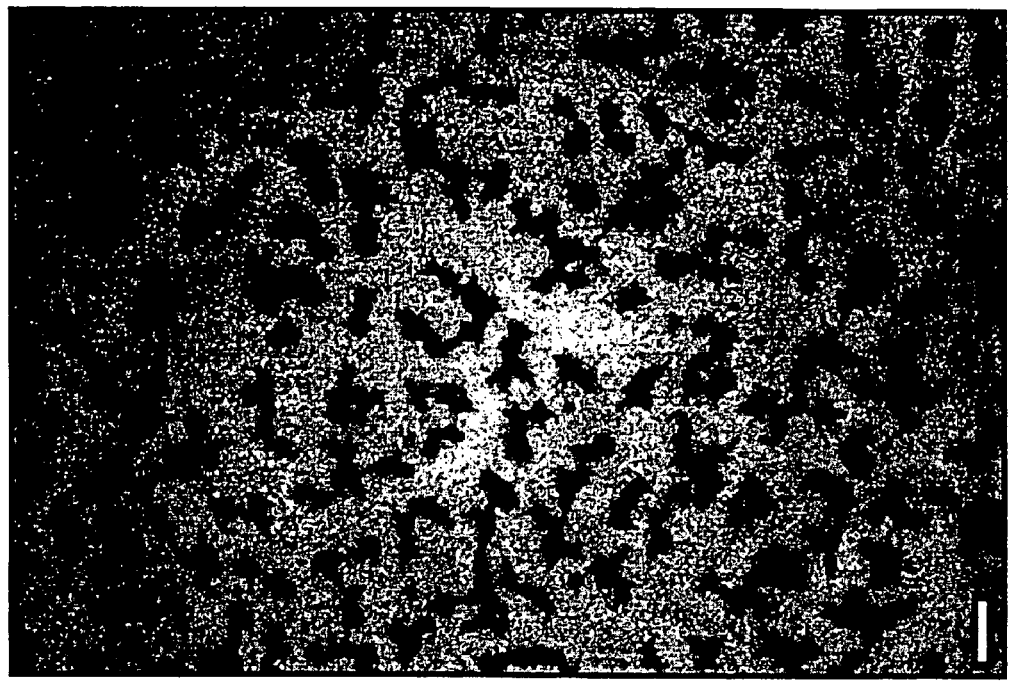
Figure 4C:
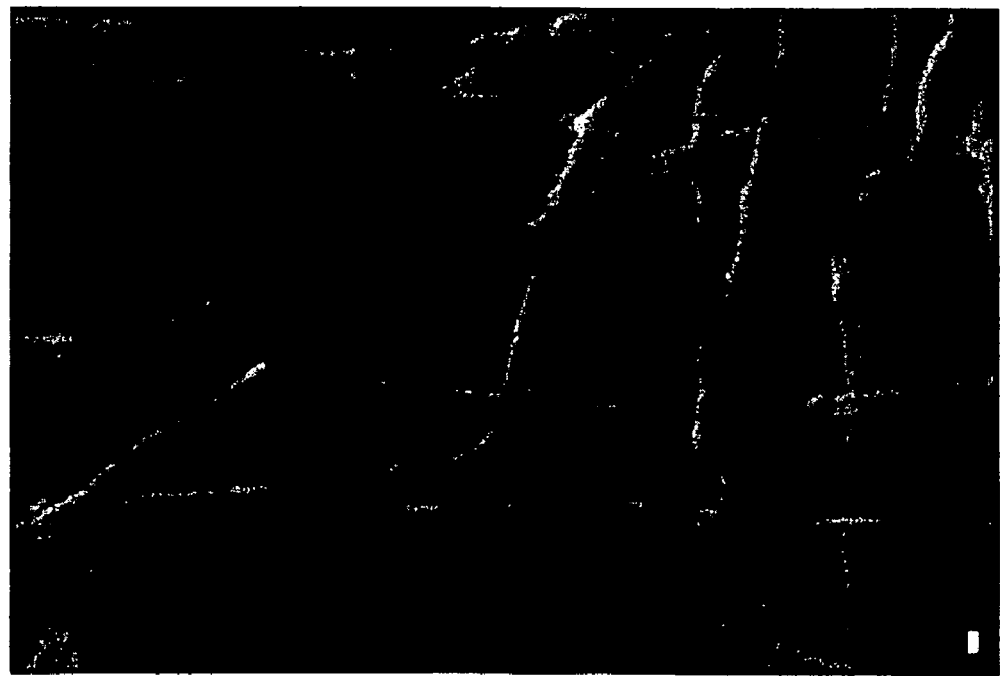
Figure 4D:
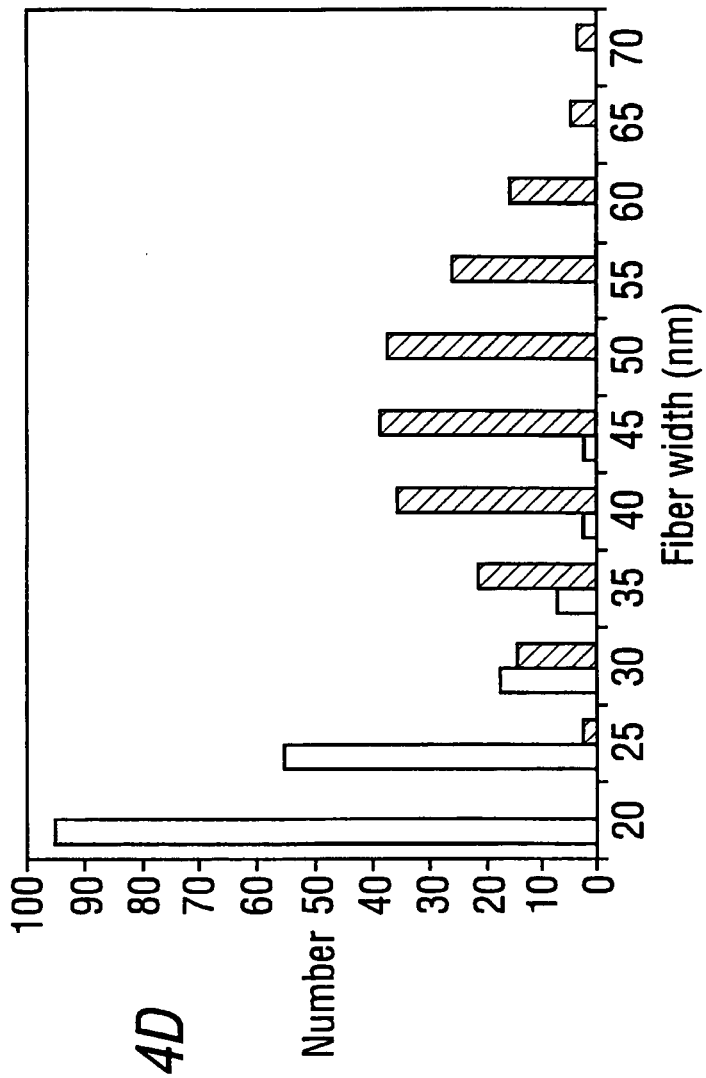
Figure 8:
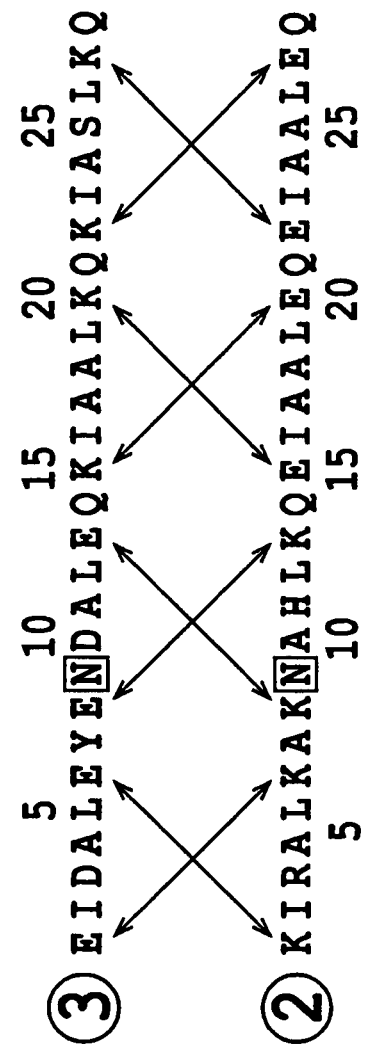
FIG. 8 shows amino acid sequences designed to form blunt-ended heterodimers.
Figure 8:
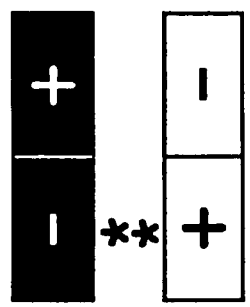

Scanning electron microscopy (SEM) of a matured mixture showed no evidence for fibre branching. Rather, the fibres were simply intertwined as if layered on top of each other (FIG. 4C). It was not possible to follow the full length of fibres due to intertwining, but they were at least several hundred microns in length. Although the density of fibres varied across the surface of the EM grid, for the matured samples at least, their diameters were quite uniform with a mean width of 43.3 (SD=9.3) nm (FIG. 4D). As the original design was for a longitudinally extended, but otherwise two-stranded coiled coil the average diameter that we might have expected was about 2 nm. Therefore, the EM data suggested that the designed two-stranded coiled-coil fibres associate laterally into higher order assemblies.

6) X-ray Fibre Diffraction

Figure 6:
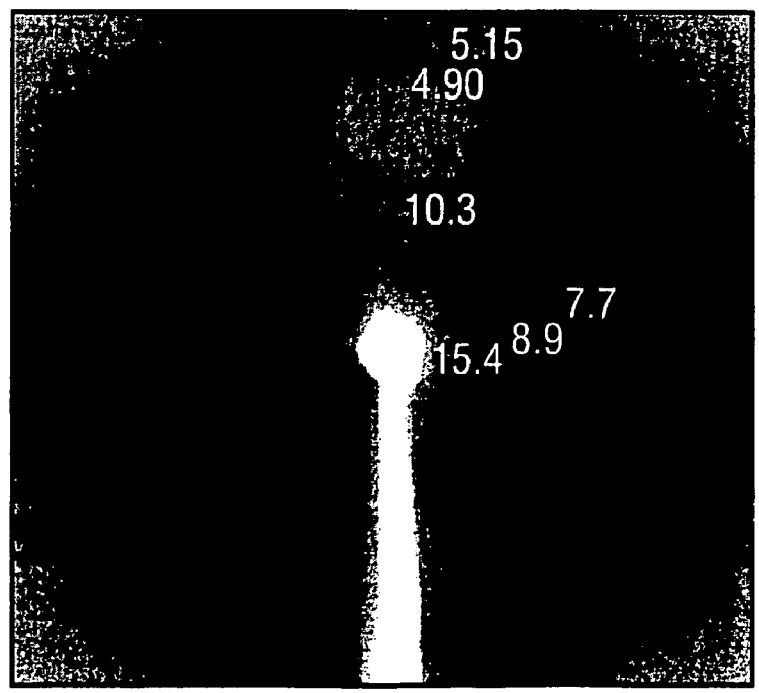
FIG. 6 is an x-ray diffraction pattern of an aligned protein fibre of the invention.

Mixtures of SAF peptides at 500 μM in 10 mM MOPS, pH 7, were incubated on ice for at least 1 h, before centrifugation at 6500 g for 5 min. Droplets of fibre-containing solutions, taken from the bottom of the centrifuged tubes, were suspended between the ends of two wax-filled capillaries and allowed to dry slowly overnight at 4° C., yielding clumps of partially aligned fibres. X-ray fibre diffraction images were collected using a Rigaku CuKα rotating anode source (wavelength 1.5418 Å) and a R-AXIS IV detector. Samples were maintained at 5° C. during data collection with cool air from a cryostream (Oxford Cryo-systems). The X-ray fibre diffraction pattern collected from SAF peptide fibres showed the following features (FIG. 6): (1) a short meridional (that is, parallel to the long fibre axis) reflection at 5.11±0.03 Å; (2) the harmonic of this 5.11 reflection at 10.19±0.05 Å; and (3) a stronger, more diffuse reflection centered at 8.8±0.15 Å on the equator. These features are consistent with α-helical coiled-coils aligned with the fibre axis. The 5.1 Å meridional reflection corresponds to the pitch of the helices within the coiled-coils. The other expected reflection on the meridian-that is, that at 1.5 Å and corresponding to the rise per residue-lies out of the resolution of the current data sets, whereas the equatorial reflection reveals the mean distance between α-helical axes. This value at 8.8 Å is less than the observed value for keratin but falls within reported ranges for dimeric coiled-coil peptides.

7) Effect of Potassium Fluoride on Protein Fibre Assembly

Molecular modeling of the SAF sequences into an extended two-stranded coiled coil also highlighted potential complementary charge interactions on the surface of the protofibrils, FIGS. 1 & 2. In accordance with this, experimentally it was found that moderate concentrations of salt inhibited protofibril and thick fibre assembly. First, CD spectra recorded for both the individual peptides and a 100 μM mixture of SAF peptide samples with 0.5 M potassium fluoride showed reduced helical CD signals and there was no evidence of "maturing" in the mixed samples (FIG. 3C). Second, the LD signal described previously for the matured 100 μM SAF peptide mixture was also lost when the experiment was repeated in the presence of salt (FIG. 3D). Finally, TEM images of a 100 μM SAF mixture also demonstrated that fibres were not formed in the presence of 0.5 M KF (FIG. 4E). FIG. 4E shows the results of TEM of a matured SAF peptide mixture at 100 μM incubated in the presence of 0.5 M KF. The inventors did not knowingly design any features into the SAF peptides to foster further association of the two-stranded coiled coils. The observation of thick fibres in SAF peptide preparations, therefore, raised the question: what interactions guided and stabilized these higher-order assemblies? The inventors therefore propose that features inherent in repeating structures of the type that they designed will naturally promote such fibre assembly (fibrillogenesis).

Consider a protofibril as depicted in FIGS. 1B and 2A. Any sequence feature presented on its surface by either, or both of the constituent peptides will be repeated at regular intervals along the protofibril. The repeat length will be equal to the length of the peptides (for SAF-p1 and SAF-p2 this was 28 residues, or about 4.2 nm). Furthermore, the motif will spiral around the protofibril tracking the superhelix of the coiled coil, which has a pitch of about 15 nm for a contiguous, heptad-based, dimeric structure. In this scenario, protofibril-protofibril interactions may be promoted if another sequence motif complementary to the first is present in the potential partner. This is because the pitches of the complementary motifs on each protofibril will match precisely. Thus, once initiated, lateral association of protofibrils—that is, fibrillogenesis—will be cemented by many regularly spaced interactions as in a crystal. As a result, the complementary interactions need only be weak as the stability of the protofibril-protofibril interaction rests on an avidity effect rather than a small number of strong interactions. Provided that the components of the assembly can make more than one type of complementary surface very extensive molecular assemblies may result. The inventors used electrostatic interactions both to direct heterodimer formation, and to promote elongation of the protofibrils (FIGS. 1 and 2). These features would also create periodic and alternating patches of charge in the protofibrils provided they are regular as envisaged (FIGS. 1B and 2B). These charged patches could guide and stabilize the higher order assemblies. Indeed, similar features have been noted in several natural fibrous proteins and have been implicated in the assembly of multi-protein filaments (J. J. Meng et al (1994) *Biol. Chem.* 269, 18679; A. D. McLachlan and M. Stewart (1976) *Mol. Biol.* 103, 271), and small synthetic peptide systems (S. G. Zhang et al (1993) *Proc. Natl. Sc. U.S.A* 90, 3334). The experiments with salt (KF) described above suggest that salt-bridges (electrostatic interaction) may be at least in part the cause of fibrillogenesis.

8) Coiled-coils Design a. For two superimposed heptads there are three possible sequence offsets of 1, 2 and 3 residue(s), which are equivalent to 6, 5 and 4-residue offsets, respectively. For a regular 3.6-residue-per-turn a-helix, these set up two hydrophobic faces with angular offsets of 100°, 160° (360-200) and 60° (360-300), respectively, around the outside of the helix. This is best seen on a helical wheel. Accounting for helical supercoiling—i.e assuming 3.5 residues per turn and using the accepted helical-wheel representation for the coiled-coil these angular offsets are altered to 103°, 154° and 51°, respectively. However, both sets of angles are over-simplifications when considering helix-helix interactions in actual coiled-coil systems because side-chain size, geometry and packing also affect the helix interfaces (Harbury, P. B. et al (1993) *Science* 262, 1401-1407; Harbury, P. B. et al (1994) *Nature* 371, 80-83; Malashkevich, V. N. et al (1996) *Science* 274, 761-765). Nonetheless, we found that many natural coiled-coil assemblies, at least, were consistent with the approximate angular offsets: Trimers could be considered as having overlapping heptads separated by 3 residues (angular offset=51/60°). Whereas, tetrameric and pentameric coiled-coils were often variations on a theme with two hepad repeats offset by 1 residue (100/103°).

b. Two heptad repeats offset by two residues: α-cylinder constructions

Sequence offsets of 2 residues are potentially more interesting than the 1- and 3-residue offsets. This is because of the possibility of placing hydrophobic (H) residues at a, c, d, and f, with c and f effectively making up the a' and d' positions of the second, offset heptad. This is represented below, where P signifies polar (non-core) residues.

```
a b c d e f g a b c d e f g       repeat 1
H P P H P P P H P P P H P P P     binary pattern 1
P P H P P H P P P H P P H P       binary pattern 2
f'g'a'b'c'd'e'f'g'a'b'c'd'e'     repeat 2
a b c d e f g a b c d e f g       assigned register
H P H H P H P H P H H P H P       overall binary
                                  pattern
```

Such sequence patterns would results in two hydrophobic seams with a wide angular separation (154/160°), which would place them roughly on opposite sides of the helix. Furthermore, it offers two possibilities for parallel helix-helix packing arrangements: syn, where two like faces—i.e a/d with a/d, or c/f with c/f—from neighbouring helices combine to produce an openα-sheet, FIG. 6a; anti, where a/d faces pair with c/f. In the anti-arrangement the structure can close to form α α-cylinder. For antiparallel pairs of helices syn-typic association should lead to cylinders, whereas sheets should be formed from anti-typic antiparallel interfaces.

c. A Natural α-Cylinder

TolC has two α-barrel-like domains (Koronakis, V. et al (2000) *Nature* 405, 914-919). Both have 12 helices contributed by 3 monomers. In the lower barrel each helix pairs with another from the same protomer to form separate supercoiled, antiparallel coiled-coils; SOCKET analysis revealed extensive antiparallel knobs into holes (KI) interactions within these pairs, but not between them. In contrast, the helices of the upper barrel appear to pack more uniformly, albeit with a slant, to describe an α-cylinder. The SOCKET output for this part of the structure revealed many fewer KIH interactions than found in the lower barrel. Furthermore, KIH interactions were not contiguous around the cylinder and, in particular, they were more extensive between helices in the same monomer, but less regular between the helices abutting the monomers. In our view, the TolC barrel represents a variation of the cylinders formed by protein structures of the invention.

Nevertheless, the inventors were able to assign heptad registers for the helices of the upper barrel unambiguously. This revealed knobs at relative a, c, d, and f positions and syn-typic association of two seams adjacent helices; i.e fully consistent with the theory outlined above.

We believe that it will be possible to constuct α-sheets and α-cylinders using helices in parallel. The use of parallel helices does have one interesting consequence for the construction of α-cylinders, however: as the pairing in these structures will be anti-typic, α residues on one helix partner c residues of a neighbouring helix at the same level in the structure. Similarly, d and f residues pair at the intervening levels. The result will be that successive helices will be translated up the helix and cylinder axes by two residues, which is equivalent to ~3 Å. Thus, attempts to construct α-cylinders from parallel helices will give spirals of helices which may or may not close. This is, however, potentially extremely interesting as it opens up possibilities for making peptide-based nanotubes as described above.

A second consideration for α-cylinder construction is the consequences of helix and coiled-coil supercoiling. The upper barrel of TolC has 12 helices. Based on a structure of parallel helices with canonical supercoiling, i.e an angular separation of 154° between the two seams in each helix, we calculated that the cylinder should close at 14 helices. However, variations in helix number are expected. One reason for this is that helices cannot supercoil in two direction simultaneously, and some distortion is required to maintain packing at both interfaces. We found structural precedents for this in the Protein Data Book PDB where tight knobs-into-holes packing was maintained (Walshaw & Woolfson, unpublished); indeed, the central helices of the 3-helix α-sheets are straight, FIG. 7b. (n.b . The slanting of the helices in the upper barrel of TolC may offer a compromise between straight and supercoiled helices). Assuming the packing of completely straight helices, the angular offset becomes 160° and 18 helices would close a cylinder. However, given that, as in 3-, 4- and 5-stranded coiled coils, side chains mediate the helix-helix contact angles other oligonmerisation states might be possible (Harbury, P. B et al (1993) *Science* 262, 1401-1407; Harbury, P. B. et al (1994) 371, 80-83; Malashkevich, V. N. et al (1996) *Science* 274, 761-765): we calculate that small adjustments in the angular offset between 144° to 162° varies the helix number from 10 to 20.

9) Formation of Protein Structures

As mentioned above, the protein structures of the invention may have various applications such as in:

Nanotubes a. This can be achieved for example by combining the aforementioned 7- and 11-residue repeats with offsets in the sequence. The effect would be eliminate the overall hydrophobic displacement. In other words, alternating heptad and hendecad repeats give an 18-residue repeat to match the α-helical repeat; in the α-helix, 18 residues span 5 helical turns exactly. It may therefore be possible to create a completely closed peptide nantotube (FIG. 5 shows part of a nanotube) In the parallel, straight helix case there would be 18 helices per turn of the "cylinder", and the rise per turn is 36 residues. Thus, a 36-residue peptide with a 7-11-7-11 repeat offset by 2 residues should form a spiral of helices the ends of which meet to close the tube. Such nanotubes maybe particularly useful in the production of nanoscale piping and plumbing. The interior of the tube may be derivatised to control the flow of different small (2-40 Å) molecules.

b. Derivitised and Branched Peptides and Peptide Templates

Figure 7:
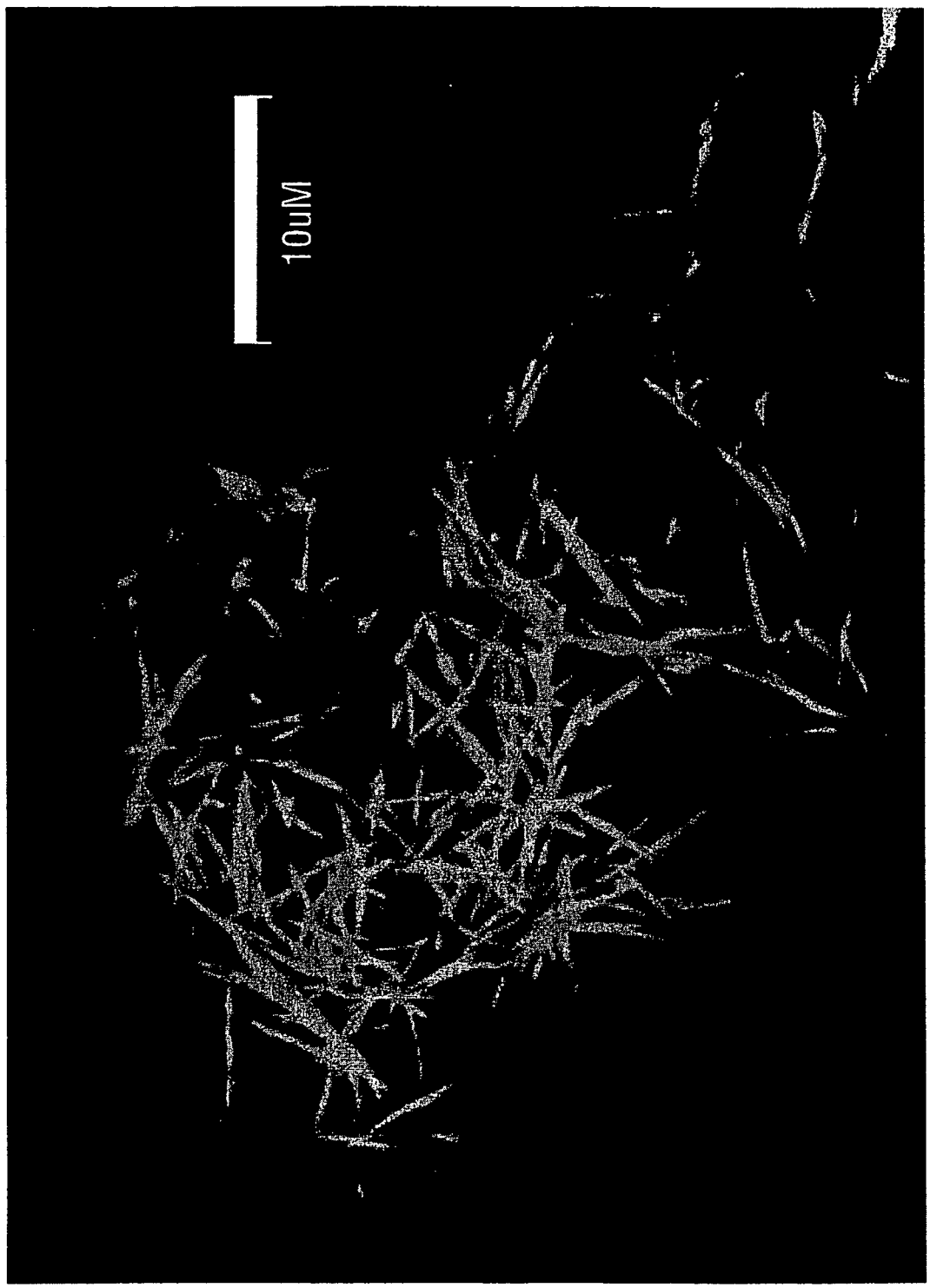
FIG. 7 is an electromicrograph showing fibres which have been derivatised through the inclusion of flurophores.

The self-assembling peptides of the invention are relatively small and synthetically accessible. Thus, non-standard derivatisable side chains may be incorporated in them. For example, the monomer units can be made with a single cysteine residue at an exterior f position. These can be used to couple small molecules and other peptides using thiol-based chemistry. A wide variety of thiol-reactive probes are available. In particular, the peptides can be tagged with fluorophores. For instance, with one peptide labelled with Fluorescein and the other with Rhodamine fibres visualised by confocal microscopy appear green and red, respectively (FIG. 7). There is a possibility for FRET between the probes, which may pack closely in the fibres, and this may confuse interpretation. To avoid this the tagged peptides can be doped into fresh, assembling SAF mixtures. Having available fluorescently labelled peptides and fibres offers another route to tracking fibre/network assembly and orientation.

To generate branched self-assembling fibres "T-shaped" conjugated peptides can be made. These are covalent heterodimers made by mixing and coupling together variants of two SAF peptides: one with a terminal cysteine and the other having a central cysteine residue. The desired products can be purified from the mix of disulphide-linked peptide by PHLC. Doping the conjugated ("T") peptides into fresh SAF mixtures should propagate fibre assembly in three dimensions as both the "bar" and the "stem" of the "T" could become incorporated in, or initiate, fibres. The resulting networks can be visualised and characterised by EM.

Peptide synthetic diblock copolymer hybrids may be produced. Suitable methods for preparing water soluble diblock copolymers using atom transfer radical polymerisation are described in X. S. Wang et al Chemical Communications 1817 (1999) and X. S Wang et al Macromolecules 33, 257 (2000).

The protein fibres of the invention may be used to template and control this polymerisation either to produce hybrid fibres or if the peptide template is subsequently disassembled and marked away, to provide routes to water soluble "fishnet" nanotubes. Other possibilities include: conjugating polymers onto preassembled peptide fibres; conjugating the polymers and peptides prior to fibre assembly; and effecting polymerisation on the pre-assembled fibres.

c. Formation of Matrices

The protein fibres of the invention may be arranged to form two and three dimensional grids and matrices respectively. One application for such matices is in the purification of biological fluids such as blood. An affinity matrix could be assembled (for example in situ in blood) to remove blood contaminants such as viruses. In the case of virus removal, a binder for the target contaminant (e.g a peptide or protein with natural or engineered affinities for a viral coat protein) can be fused to a peptide monomer units in the protein structure of the invention. The matrix can then be removed from blood along with any bound contaminants by light centrifugation. For example, it is estimated that a 100 nm length of fibre would have a mass of $\geq 12$ MDa which would readily be removed. Such affinity matrices have a number of advantages over larger naturally occurring proteins. In the assembled matrices any binders are aligned to give high effective avidities for the targeted molecules.

d. Other Applications

Other applications for protein structures in accordance with the invention include:

i. preparation of organised networks for seeding the crystalisation of biomolecules for X-ray crystallography;

ii. using ordered fibres toprmote cell growth for tissue engineering;

iii. the construction of nanoscale molecular sieves iv. the preparation of nanoscale molecular grids/scaffolds that could be used as supports for a variety of functional small or macromolecules.

v. functionalised grids and networks could be used in, for example, catalysis, affinity-sieving/purification of biological fluids and other research solutions, the recruitment of endogenous molecules and co-factors to promote tissue repair and tissue engineering in general.

vi. to create novel lab-on-chip technologies, peptide self-assembly could be combined with lithography as follows.

Lithography and related techniques can be used to pattern a variety of surfaces with channels, which can be made of a suitable size (e.g 20-100 nm wide and deep) to accommodate peptide fibres. These can then be used to direct the assembly of the fibres from solutions mixed directly on the surfaces. Furthermore, using well-established chemistry, the inventors envisage funtionalising the peptide fibres with a variety of small molecules and other proteins. This proposed combination of peptide design, self-assembly and lithography should allow the development of ordered arrays of functional polymers on specific surfaces.

vii. Assembled fibres could also be used as fine (therefore, high resolution) tips in AFM (atomic force microscopy) the current limit is about 10-25 nm using carbon nanotubes.

The invention claimed is:

1. A method of forming a protein structure comprising:

mixing a plurality of copies of a first peptide monomer unit with a plurality of copies of a second peptide monomer unit, whereby the plurality of copies of the first peptide monomer unit and the plurality of copies of the second peptide monomer unit self-assemble to form a heterodimer comprising a first strand comprising the plurality of copies of the first peptide monomer unit and a second strand comprising the plurality of copies of the second peptide monomer unit, wherein each of the first and second monomer units comprise a heptad repeat motif (with positions in each of the motifs represented by abcdefg), wherein each of the heptad repeat motif has a pattern of hydrophobic (H) and polar (P) amino acid residues represented by HPPHPPP, wherein the sequence of the first strand and the sequence of the second strand are non-identical, and wherein said first and second monomer units together comprise a pair of amino acid residues selected from the group consisting of: a pair of asparagines, a pair of arginines, and a pair of lysines, wherein one amino acid residue of each pair is in an "a" position of a heptad repeat motif on each of the first and second peptide monomer units, and wherein at least one charged amino acid residue of the first peptide monomer unit is arranged to attract an oppositely-charged amino acid residue of the second peptide monomer unit, and wherein the pair of amino acid residues in the "a" positions are in motifs that are in different ordinal positions within the first and second peptide monomer units such that upon heterodimerization at least one motif on each strand overhangs the heterodimer, whereby the first strand and the second strand form a staggered, parallel, heterodimer, coiled-coil structure.

2. The method of claim 1 wherein at least two charged amino acid residues of the first peptide monomer unit are arranged to attract an oppositely-charged amino acid residue of the second peptide monomer unit.

3. The method of claim 1 wherein at least three charged amino acid residues of the first peptide monomer unit are arranged to attract an oppositely-charged amino acid residue of the second peptide monomer unit.

4. The method of claim 1 wherein at least four charged amino acid residues of the first peptide monomer unit are arranged to attract an oppositely-charged amino acid residue of the second peptide monomer unit.

5. The method of claim 1 wherein at least five charged amino acid residues of the first peptide monomer unit are arranged to attract an oppositely-charged amino acid residue of the second peptide monomer unit.

6. The method of claim 1 wherein the g position in the repeat motif is an amino acid selected from the group consisting of lysine or glutamate.

7. The method of claim 1 wherein the pair of amino acid residues in the a position within a heptad repeat motif on the first and second peptide monomer units are a pair of asparagines.

8. The method of claim 1 wherein the b position in the repeat motif is an amino acid selected from the group consisting of alanine or arginine.

9. The method of claim 1 wherein the c position in the repeat motif is an alanine.

10. The method of claim 1 wherein the d position in the repeat motif is a leucine.

11. The method of claim 1 wherein the e position in the repeat motif is an amino acid selected from the group consisting of lysine or glutamate.

12. The method of claim 1 wherein the f position in the repeat motif is an amino acid selected from the group consisting of alanine, glutamine, or glutamate.

13. The method of claim 1 wherein the first and second peptide monomer units are synthesized using solid-phase methods and Fmoc chemistry.

14. The method of claim 1 wherein said first and second polypeptide strands consist solely of first or second monomer units respectively.

15. The method of claim 1 wherein said polypeptide strands consist solely of repeat motifs.

16. The method of claim 1 wherein the g position is selected from the group consisting of lysine or glutamate; the b position is selected from the group consisting of alanine or arginine; the c position is an alanine; the d position is a leucine; the e position is selected from the group consisting of lysine or glutamate; and the f position is selected from the group consisting of alanine, glutamine, or glutamate.

17. The method of claim 1 further comprising the step of:
    maturing the staggered, parallel, heterodimer, coiled-coil structure by incubation to form fibers.

18. The method of claim 17 wherein the incubation is conducted for 1 hour at 5° C.

19. The method of claim 1 wherein the first and second peptide monomer units are mixed in equal proportions.

* * * * *